(12) United States Patent
Emori et al.

(10) Patent No.: US 10,058,279 B2
(45) Date of Patent: Aug. 28, 2018

(54) SLEEP AND ACTIVITY AMOUNT DISPLAY PROGRAM, DEVICE, SYSTEM, AND METHOD

(71) Applicant: OMRON HEALTHCARE CO., LTD., Muko-shi, Kyoto (JP)

(72) Inventors: Yasuko Emori, Kyoto (JP); Yoko Kanemitsu, Kyoto (JP); Feilang Tseng, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 461 days.

(21) Appl. No.: 14/816,174

(22) Filed: Aug. 3, 2015

(65) Prior Publication Data
US 2015/0339792 A1    Nov. 26, 2015

Related U.S. Application Data

(63) Continuation of application No. PCT/JP2014/055107, filed on Feb. 28, 2014.

(30) Foreign Application Priority Data

Mar. 1, 2013   (JP) ................. 2013-040299

(51) Int. Cl.
*G16H 15/00*    (2018.01)
*A61B 5/00*    (2006.01)
(Continued)

(52) U.S. Cl.
CPC .......... *A61B 5/4806* (2013.01); *A61B 5/1118* (2013.01); *A61B 5/742* (2013.01); *A61B 5/743* (2013.01); *G06Q 50/22* (2013.01); *G16H 15/00* (2018.01); *A61B 5/022* (2013.01); *A61B 5/4866* (2013.01); *G06F 19/3481* (2013.01); *Y02A 90/22* (2018.01); *Y02A 90/26* (2018.01)

(58) Field of Classification Search
CPC .................................. A61B 5/02; G16H 15/00
See application file for complete search history.

(56) References Cited

U.S. PATENT DOCUMENTS

2004/0111041 A1*   6/2004   Ni ........................ A61B 5/0205
600/544

FOREIGN PATENT DOCUMENTS

| JP | 2003-339674 A | 12/2003 |
|---|---|---|
| JP | 2005-124858 A | 5/2005 |

(Continued)

OTHER PUBLICATIONS

Official Communication issued in International Patent Application No. PCT/JP2014/055107, dated May 27, 2014.

*Primary Examiner* — John A Pauls
(74) *Attorney, Agent, or Firm* — Keating and Bennett, LLP (57) ABSTRACT

Provided is a sleep and activity amount display program that allows easy checking of sleep data along with activity amount data for each time period of a certain day. The sleep and activity amount display program includes a step of obtaining sleep data of a user from a sleep measurement device; a step of obtaining activity amount data of a user from an activity measurement device; a step of creating a time display image divided into time slots that each indicate a predetermined range of time; and a step of plotting a getting-up time and a bedtime included in the sleep data as well as the activity amount data on the time slots of the time display image.

8 Claims, 7 Drawing Sheets

(51) Int. Cl.
*G06Q 50/22* (2018.01)
*A61B 5/11* (2006.01)
A61B 5/022 (2006.01)
G06F 19/00 (2018.01)

(56) References Cited

FOREIGN PATENT DOCUMENTS

| | | |
|---|---|---|
| JP | 2007-222276 A | 9/2007 |
| JP | 2009-233027 A | 10/2009 |
| JP | 2010-148829 A | 7/2010 |
| JP | 2012-147989 A | 8/2012 |
| WO | 2010/146811 A1 | 12/2010 |

* cited by examiner

SLEEP AND ACTIVITY AMOUNT DISPLAY PROGRAM, DEVICE, SYSTEM, AND METHOD

BACKGROUND OF THE INVENTION

1. Field of the Invention

The present invention relates to a program, device, system, and method for displaying sleep data and activity amount data of a user.

2. Description of the Related Art

Conventionally, there are known to be devices that measure a user's sleep, as well as devices, methods, and the like for displaying the results of such measurement. JP 2010-148829A and JP 2003-339674A disclose storing bedtimes and getting-up times for a predetermined number of days and displaying a sleep time period for each date as a band graph.

Also, there are known to be a device for measuring data regarding an activity amount and the like, which significantly influence sleep quality, as well as a device, method, and the like for displaying the results of such measurement. JP 2007-222276A discloses obtaining sleep data using an all-night measurement terminal, obtaining activity data throughout a day using a mobile measurement terminal, and displaying several days'-worth of exercise and sleep points for each date as a bar graph.

SUMMARY OF THE INVENTION

Sleep quality is deeply related to daily lifestyle habits, and in order for a user to look back at data relating to his or her own sleep state so as to improve his or her lifestyle habits, it is important to correctly recognize the current state of his or her sleep and lifestyle habits and be aware of any problems.

For example, it is known that being in an active state before going to bed has a significant influence on sleep quality. More specifically, it is known that if strenuous exercise is performed before going to bed, falling asleep will be delayed and it is less likely that the sleep will be satisfying. However, it is not possible to understand problems regarding these kind of lifestyle habits by merely checking sleep data each day as well as the integrated value of the total activity amount for that day. For this reason, it is desired that a user can easily check his or her sleep data each day along with his or her activity amount for each time period of that day.

The present invention has been made in consideration of the foregoing circumstance, and it is an object thereof to provide a sleep and activity amount display program that allows easy checking of sleep data as well as activity amount data for each time period of a day. In addition, it is an object thereof to provide a sleep and activity amount display device, system, and method.

A sleep and activity amount display program according to the present invention includes: a step of obtaining sleep data of a user from a sleep measurement device; a step of obtaining activity amount data of a user from an activity measurement device; a step of creating a time display image divided into time slots that each indicate a predetermined range of time; and a step of plotting a getting-up time and a bedtime included in the sleep data as well as the activity amount data on the time slots of the time display image.

Preferably, the sleep and activity amount display program further includes: a step of obtaining meal data relating to a meal of a user; and a step of plotting a meal time included in the meal data on the time slots of the time display image.

Preferably, the sleep and activity amount display program further includes: a step of displaying a predetermined time range before the bedtime as a relax zone on the time slots of the time display image.

Preferably, the time display image is a display image in the form of a wave with a period of 24 hours.

A sleep and activity amount display device according to the present invention is a device on which one of the above-described sleep and activity amount display programs is installed.

A sleep and activity amount display system according to the present invention includes: a server, a sleep measurement device, an activity measurement device, and a display terminal connected via a network. Also, sleep data of the user measured by the sleep measurement device is transmitted to the server and accumulated in the server. Also, activity amount data of a user measured by the activity measurement device is transmitted to the server and accumulated in the server. Also, the server creates a display image divided into time slots that each indicate a predetermined time range, the display image displaying a getting-up time and a bedtime included in the sleep data, as well as the activity amount data on the time slots. Also, the display image created by the server is transmitted to the display terminal and is displayed on the display terminal.

A sleep and activity amount display method according to the present invention includes: a step of obtaining sleep data of a user from a sleep measurement device; a step of obtaining activity amount data of a user from an activity measurement device; a step of creating a time display image divided into time slots that each indicate a predetermined range of time; and a step of plotting a getting-up time and a bedtime included in the sleep data as well as the activity amount data on the time slots of the time display image.

According to the present invention, there is an advantage in that the user can easily check sleep data as well as activity amount data for each time period of a day.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

A configuration of a system, a display image, and operations of a program will be described in order hereinafter according to an preferred embodiment of the present invention.

Figure 1:
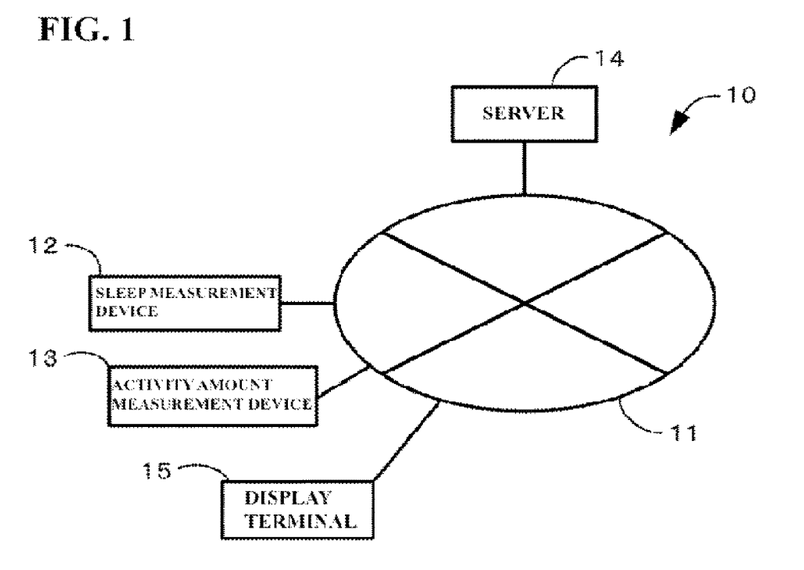
FIG. 1 is a diagram showing an example of an overall configuration of a sleep and activity amount display system.

FIG. 1 shows an overall configuration of a sleep and activity amount display system of the present preferred embodiment. A sleep and activity amount display system. 10 has a server 14, asleep measurement device 12, an activity amount measurement device 13, and a display terminal 15 that are connected via a network 11 such as the Internet or a LAN.

Figure 2:
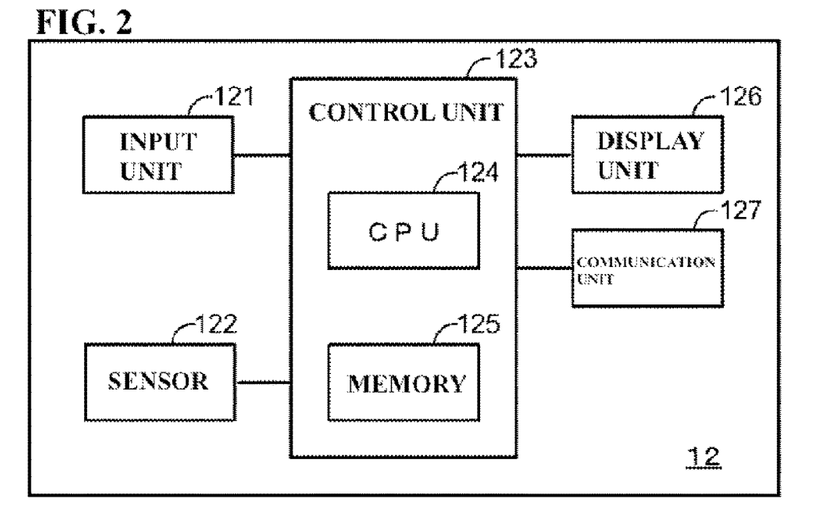
FIG. 2 is a diagram showing an example of a configuration of a sleep measurement device.

FIG. 2 shows a configuration of the sleep measurement device 12. The sleep measurement device 12 has an input unit 121, a sensor 122, a control unit 123, a display unit 126, and a communication unit 127. The input unit 121 is constituted by a group of buttons or the like, and receives instructions from a user for measurement start/end, data transmission, and the like. The sensor 122 detects the sleep state of the user. The control unit 123 has a CPU 124 and a memory 125 and performs overall control of the sleep measurement device 12. Programs to be executed by the CPU 124 and sleep data are stored in the memory 125. The display unit 126 shows a simple display of the content of instructions from the user, the content of various settings, sleep data, and the like to the user. The communication unit 127 transmits sleep data to the server 14.

There is no particular limitation to the type of the sensor 122, and a sensor that can detect bodily movement of a user, such as an acceleration sensor, an image sensor, a radio wave sensor, or an ultrasound sensor, is preferably used. Based on a signal from the sensor 122, the CPU 124 generates sleep data relating to the sleep state of the user and stores it in the memory 125. There is no particular limitation on the content of the sleep data as long as it is possible to understand the sleep state of the user therefrom. For example, bodily movement data for each predetermined time slot (e.g., 1 minute) may be used, or levels of sleep depth obtained by calculation based on the bodily movement data, or the like may be used thereas. The CPU 124 may furthermore obtain times of going to bed, falling asleep, getting up, and the like from the sleep data and include them in the sleep data.

The communication unit 127 transmits the sleep data to the server 14 via the network 11 according to an instruction from the user, or when sleep measurement ends. At that time, the sleep data may be transmitted to the server 14 due to the communication unit 127 being directly connected to the network 11, or it may be first transmitted from the communication unit 127 to a personal computer, a mobile terminal, or the like and then transmitted to the server 14 due to the personal computer, mobile terminal, or the like being connected to the network 11. If transmission cannot be completed for some reason, the sleep data will continue to be stored in the memory 125 until transmission is subsequently performed and transmission is completed.

Also, an alarm clock function can be provided in the sleep measurement device 12. In this case, the planned getting-up time of a user can be received by the input unit 121, and the planned getting-up time of a user can be transmitted from the communication unit 127 to the server 14 as part of the sleep data.

Figure 3:
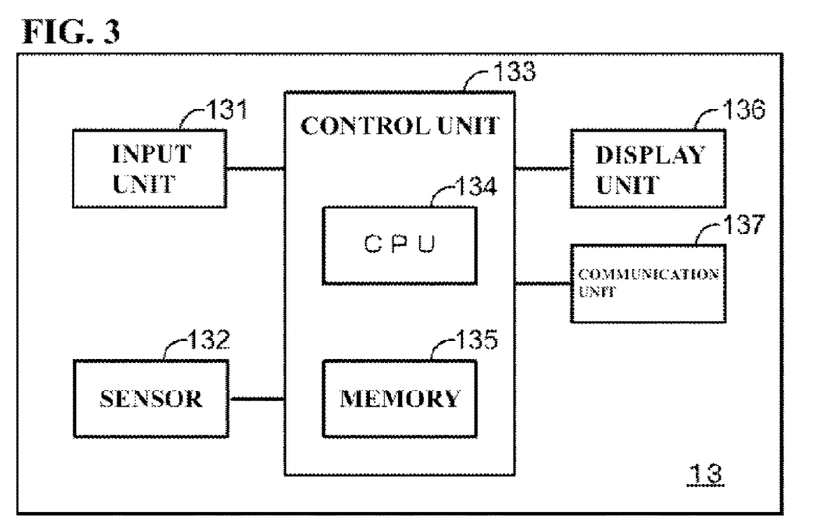
FIG. 3 is a diagram showing an example of a configuration of an activity amount measurement device.

FIG. 3 shows a configuration of the activity amount measurement device 13. The activity amount measurement device 13 has an input unit 131, a sensor 132, a control unit 133, a display unit 136, and a communication unit 137. The input unit 131 is constituted by a group of buttons or the like, and receives instructions from a user for measurement start/end, data transmission, and the like. The sensor 132 detects the activity of the user. The control unit 133 has a CPU 134 and a memory 135 and performs overall control of the activity amount measurement device 13. Programs to be executed by the CPU 134 and activity amount data are stored in the memory 135. The display unit 136 shows a simple display of the content of instructions from the user, the content of various settings, activity amount data, and the like to the user. The communication unit 137 transmits the activity amount data to the server 14.

There is no particular limitation on the type of the sensor 132, and a sensor that can detect the activity state of the user, such as an acceleration sensor, can be used. Based on a signal from the sensor 132, the CPU 134 generates activity amount data relating to the activity state of the user and stores it in the memory 135. The content of the activity amount data is a number of steps or expended calories. Note that a simple integrated amount over a long time such as an entire day, which is obtained using a classic pedometer or an activity amount meter, is insufficient, and it needs to be at least an integrated amount for each predetermined time slot (e.g., 10 minutes).

The communication unit 137 transmits the activity amount data to the server 14 via the network 11 according to an instruction from the user, or the like. At that time, the activity amount data may be transmitted to the server 14 due to the communication unit 137 being directly connected to the network 11, or it may be first transmitted from the communication unit 137 to a personal computer, a mobile terminal, or the like and then transmitted to the server 14 due to the personal computer, mobile terminal, or the like being connected to the network 11. If transmission cannot be completed for some reason, the sleep data will continue to be stored in the memory 135 until transmission is subsequently performed and transmission is completed.

Figure 4:
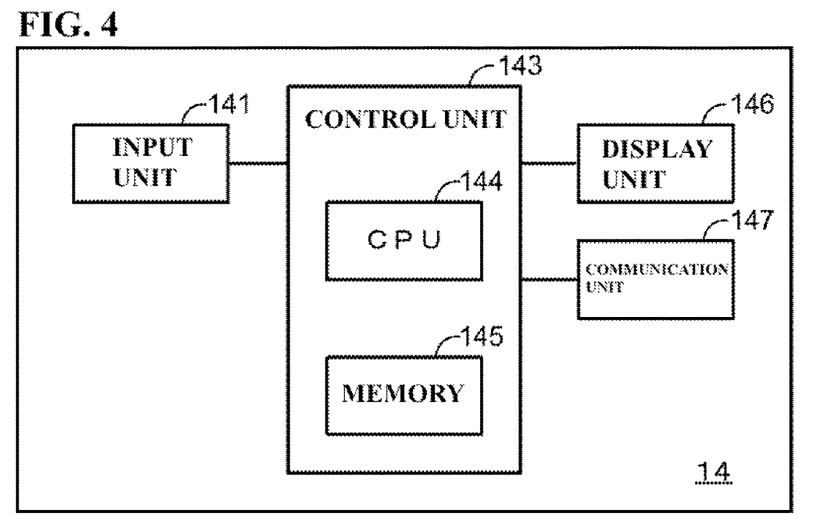
FIG. 4 is a diagram showing an example of a configuration of a server.

FIG. 4 shows a configuration of the server 14. The server 14 has an input unit 141, a control unit 143, a display unit 146, and a communication unit 147. The input unit 141 receives input from a keyboard or the like and is mainly used during maintenance of a program, or the like. The control unit 143 has a CPU 144 and a memory 145, performs overall control of the server 14, and creates a sleep and activity amount display image by executing a sleep and activity amount display program. Programs to be executed by the CPU 144, various types of data such as the sleep data and activity amount data, various setting tables, and the like are stored in the memory 145. The display unit 146 displays messages and the like to an operator and is mainly used during maintenance of a program or the like. The communication unit 147 receives the sleep data from the sleep measurement device 12, receives the activity amount data from the activity amount measurement device 13, and transmits the created sleep and activity amount display image to the display terminal 15. Asleep and activity amount display image means an image obtained by plotting the sleep data and the activity amount data on a time display image divided into time slots that each indicate a predetermined time range.

If the sleep data received by the communication unit 147 from the sleep measurement device 12 is bodily movement data, sleep depth data, or the like and does not explicitly include a getting-up time and a bedtime, the CPU 144 obtains the getting-up time and the bedtime by analyzing the received data.

Figure 5:
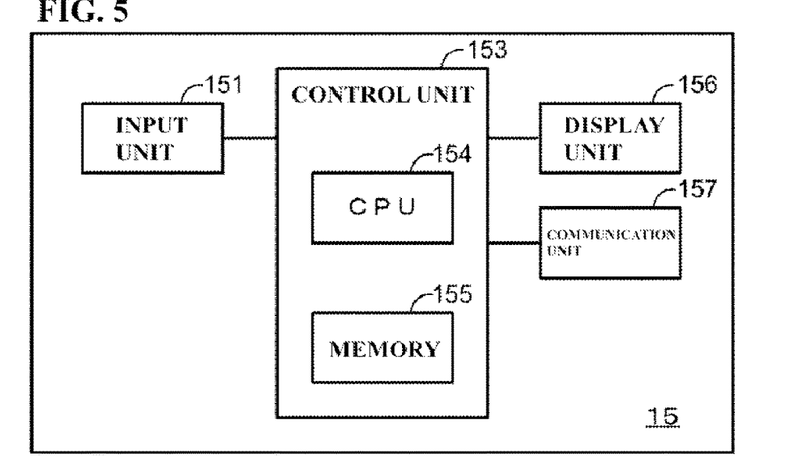
FIG. 5 is a diagram showing an example of a configuration of a display terminal.

FIG. 5 shows a configuration of the display terminal 15. The display terminal 15 has an input unit 151, a control unit 153, a display unit 156, and a communication unit 157. The input unit 151 is constituted by a group of buttons or the like, and receives instructions from a user for receiving a sleep and activity amount display screen, and the like. The control unit 153 has a CPU 154 and a memory 155 and performs overall control of the display terminal 15. The communication unit 157 receives the sleep and activity amount display screen from the server 14, and the display unit 156 displays the image to the user. It is possible to use various types of information devices such as personal computers or smartphones as the display terminal 15.

Next, a display image of the present preferred embodiment will be described.

Figure 6:
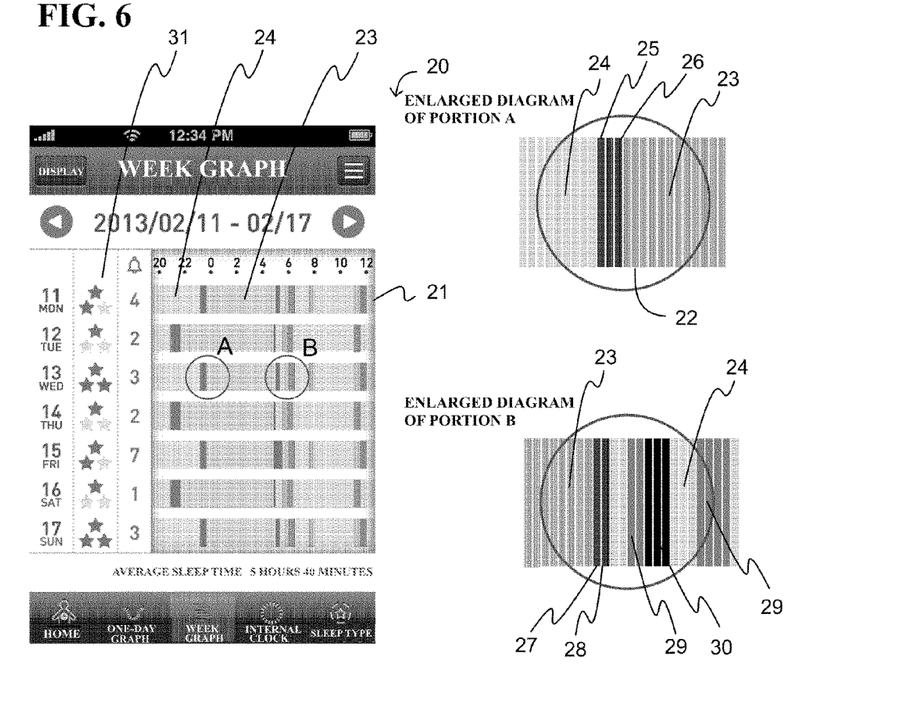
FIG. 6 is a diagram showing an example of a sleep and activity amount display image.

FIG. 6 shows an example of a sleep and activity amount display image 20 created according to the present preferred embodiment. With reference to FIG. 6, one week's-worth of time display images 21, in which each horizontal band graph spans from 8:00 pm to 2:00 pm within a period of 24 hours and seven band graphs are aligned vertically, are displayed. The time display images 21 are divided into time slots 22 that each indicate a predetermined time range. For example, regarding the time slots 22, each tick mark is obtained by dividing each hour into six equal portions and indicates a 10-minute time interval. Time slots for sleep time 23 and non-sleep time 24 are displayed using different colors in the time display image 21.

In FIG. 6, the period from the time slot corresponding to a bedtime 25 to the time slot corresponding to a falling asleep time 26 for each day is colored darkly. The "falling asleep period" indicates a period from the time when the sleep measurement device is set in preparation for going to sleep to the time when the user actually falls asleep. Also, the period from the time slot corresponding to the planned getting-up time 27 to the time slot corresponding to the getting-up time 28 in each day is colored darkly. The "period for getting up" indicates the period from the alarm time set by the user to the time when the alarm is finally stopped after sleep is extended using a snooze function or the like, or in other words, the time of getting up.

Also, in FIG. 6, the activity amount data is plotted in several time slots for the non-sleep time. Specifically, time slot 29, during which medium-intensity activity was performed, and time slot 30, during which high-intensity activity was performed, are indicated by different shades of the same color.

Furthermore, FIG. 6 displays a refreshment level (level of sleep satisfaction according to user self-evaluation) 31 evaluated using three stages. The refreshment level can be input by the user from the sleep measurement device 12 or the display terminal 15 and be transmitted to the server 14. In addition to information such as sleep duration and turning over during sleep, objective data such as meals and exercise and subjective evaluations relating to sleep that is actually experienced by the user are displayed. This makes it easier to understand the relationship between the two, and the user can be made aware, thus raising the level of user understanding and satisfaction regarding the result. Because of this, an effect such that the user's desire to improve his or her habits increases can be expected.

Figure 7:
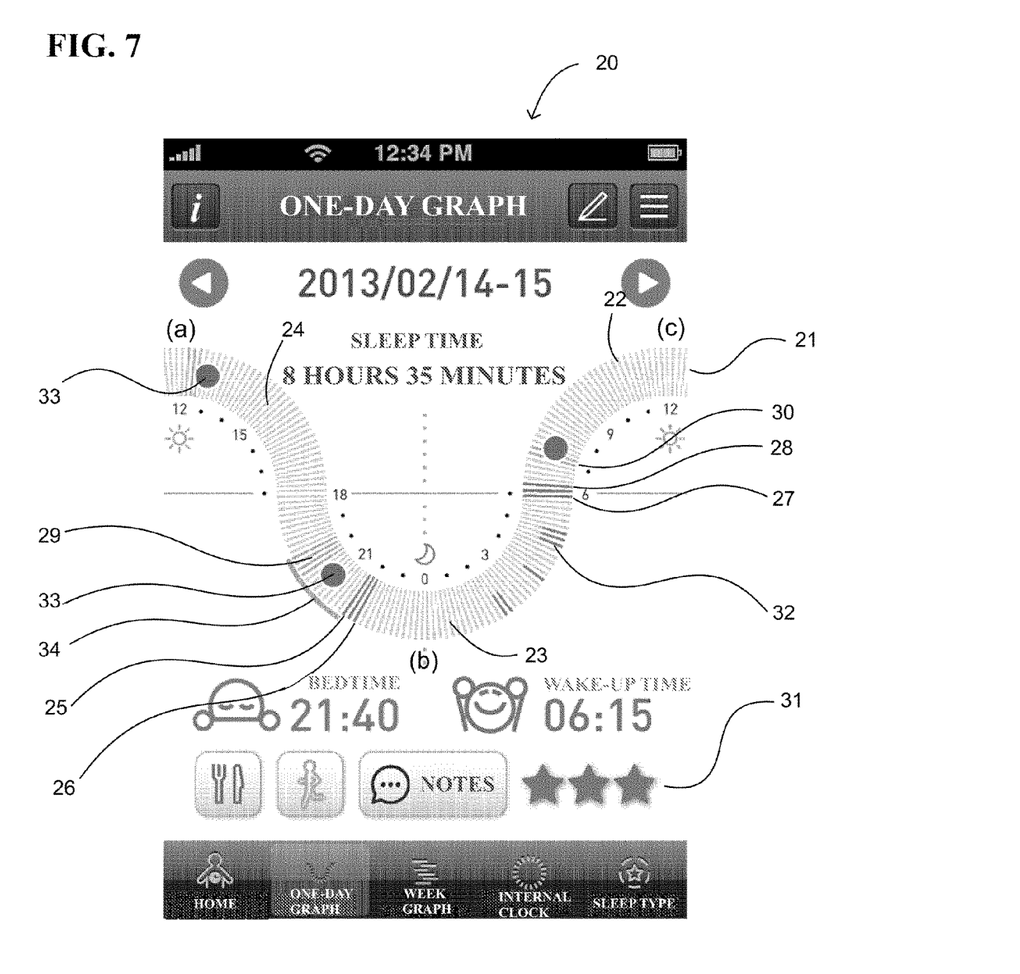
FIG. 7 is a diagram showing another example of a sleep and activity amount display image.

FIG. 7 shows another example of asleep and activity amount display image 20 created according to the present preferred embodiment. With reference to FIG. 7, the time display image 21 has a wave shape with a period of 24 hours. More specifically, the time display image 21 in FIG. 7 is such that the time around noon (a) of a certain day is in the upper left portion of the screen, the time display image 21 proceeds downwardly right with the progression of time, reaches its lowest point near the middle of the screen at 0 hours midnight (b), and proceeds upwardly right with the progression of time, and the time around noon (c) of the next day is in the upper right portion of the screen. According to this, the sleep period is displayed without being divided. Thus, the sleep information, which is bodily information to be displayed, has the same period as the time display image 21, whereby the start and end points of the image can be selected appropriately so as to display the sleep time period without dividing it. Therefore, an effect is achieved in which it is easy to understand the sleep state. Furthermore, when the display screen in FIG. 1 is switched to the data for the previous day or earlier or for the next day or later, the same times are displayed at the same height. Therefore, it is easy to understand the continuity of time. Preferably, the display screen in FIG. 7 can allow scrolling in the horizontal direction. This makes it possible to more intuitively understand the continuity of time when checking the data for the previous day or earlier or for the next day or later.

In FIG. 7, as for the time slots 22, in one example, each tick mark is obtained by dividing one hour into four equal portions and indicates a 15-minute time interval. Similarly to FIG. 6, the sleep time 23 and the non-sleep time 24 are displayed using different colors, the bedtime 25, the falling asleep time 26, the planned getting-up time 27, the getting-up time 28, and the activity amount data 29 are plotted, and the refreshment level 31 is displayed on the time display image 21. In FIG. 7, a time 32 when turning over is performed during sleep is furthermore plotted.

Furthermore, in FIG. 7, a time when the user has a meal is plotted by displaying a meal mark 33 at that time slot. A meal time can be input by the user from the display terminal 15 or the like and transmitted to the server 14. It is known that eating habits, along with the amount of activity, have a significant influence on sleep quality each day. For this reason, by showing the meal mark 33 and the sleep data at the same time, it is possible to allow the user to recognize the quality of his or her eating habits so as to increase his or her desire to improve them.

Furthermore, in FIG. 7, the two hours before bedtime are displayed as a relax zone 34. It is known that actions in a certain range of time before the bedtime 25 has a significant influence on sleep quality. For example, it is known that if the user exercises strenuously or has a meal in this range of time, falling asleep will be delayed and it is less likely that the sleep will be satisfying. There are various opinions on the size of this time range, and it is said to be 1 hour or 3 hours, but in FIG. 7, in one example, the two hours before bedtime are used as the relax zone.

As described above, it is required that the getting-up time and the bedtime included in the sleep data are displayed on the sleep and activity amount display image. This is because these two times are particularly important when the user looks back on his or her sleep performance and lifestyle habits. Other sleep data displayed on the sleep and activity amount display image can be selected as needed from the falling asleep time, the sleep depth, turning-over times, a waking time, planned getting-up time, and the like. It is particularly preferably to display the falling asleep time along with the bedtime, and the planned getting-up time along with the getting-up time, since the user can thereby know the amount of time needed for falling asleep and the amount of time needed for getting up. Thus, providing information that is relevant to the user's sleep is useful for improving the user's sleep rhythm.

Also, it is required that the activity amount data is displayed on the sleep and activity amount display image. The number of steps, expended calories, and the like can be used as the activity amount data. Regarding the method for displaying the activity amount data, a value such as the expended calories may be displayed as-is, or, as in FIGS. 6 and 7, it is possible to display whether or not activity within a pre-determined intensity range has been performed.

It is preferable that the sleep data and activity amount data are displayed in association with the color, number, or area of a graphic, or a combination thereof. In FIGS. 6 and 7, they are displayed in association with the shade of the color, but there is no limitation to this, and it is possible to change the color according to the type of data or change the length of the colored portion according to the activity amount of that time slot. This makes it possible for the user to intuitively understand the measurement result.

Also, it is preferable that the time display image is in the form of a wave with a 24-hour period, as shown in FIG. 7. Compared to the bar graph shown in FIG. 6, it is easier to understand the continuity between the time period in which the result is shown and the preceding and following time periods at a glance with a wave-shaped graph, and therefore perceptibility is improved for the user. In actuality, if the screen is made scrollable as a preferred mode, it is possible to check that the time display image is continuous without interruption in the past and future by scrolling through the screen. Furthermore, for example, by forming the time display image such that it moves toward the upper portion of the screen before noon and moves downward after noon, daytime is displayed in the upper portion of the screen and nighttime is displayed in the lower portion of the screen, and it is possible to more intuitively recognize which portions of the display image correspond to daytime and which portions correspond to nighttime, and to recognize the time period in 24 hours in which the user's sleep time is distributed. Since lifestyle habits such as sleep and a person's activity have a 24-hour cycle, it is possible for the user to more intuitively recognize the measurement results of sleep and activity amount and to more easily understand the relationship between the two by using a wave-shaped graph with a period of 24 hours.

Note that the shape of the wave-shaped graph is not limited to being a shape obtained by connecting half-circles alternatingly, as shown in FIG. 7, and it is possible to use a trigonometric function graph, a trigonometric waveform, a rectangular waveform, or other various types of wave shapes that change periodically on the screen. Also, the direction in which the wave-shaped graph extends in accordance with the elapse of time is not limited to being the horizontal direction shown in FIG. 7, and may be the vertical direction, or an oblique direction. That is to say, it is sufficient that continuity of the flow of time can be brought to mind by taking one period of a shape with periodicity and displaying it on one screen.

Next, operations of a program of the present preferred embodiment will be described.

Figure 8:
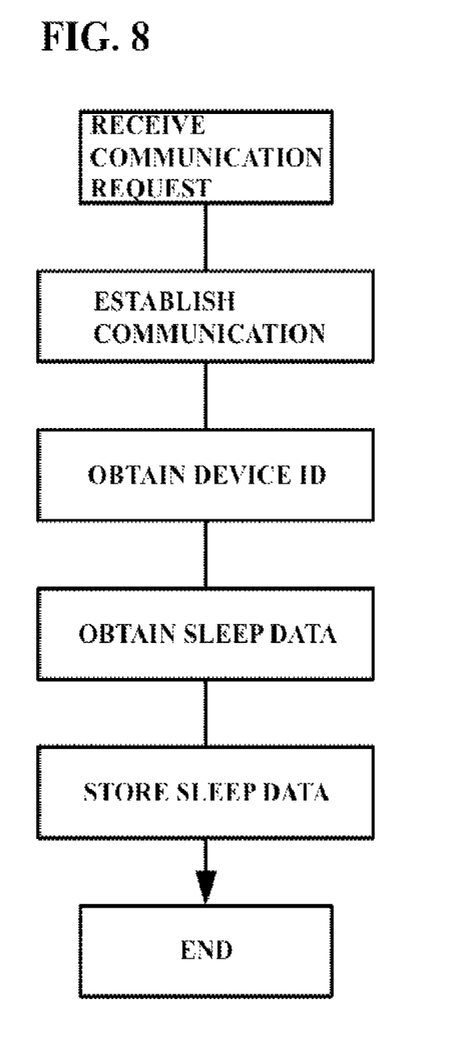
FIG. 8 is a diagram showing an example of an operation by which a server obtains sleep data.
Figure 9:
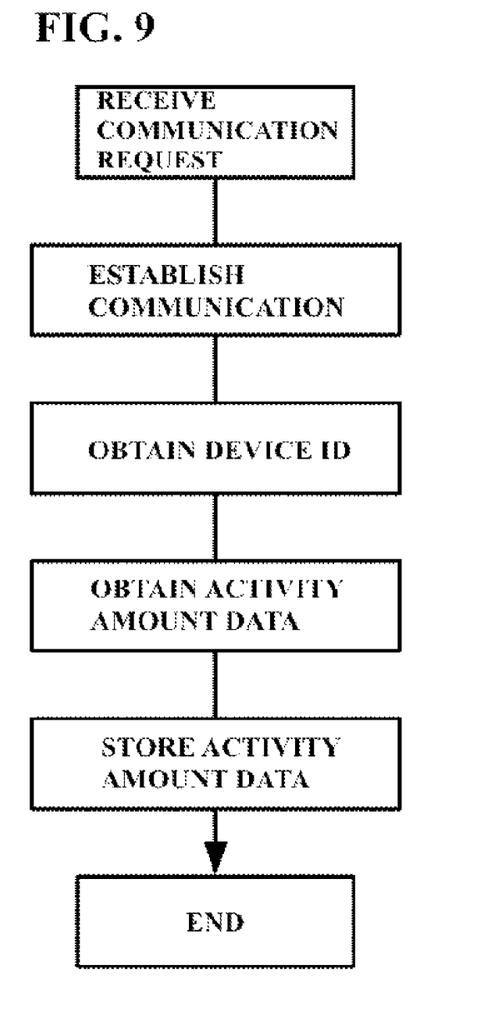
FIG. 9 is a diagram showing an example of an operation by which a server obtains activity amount data.
Figure 10:
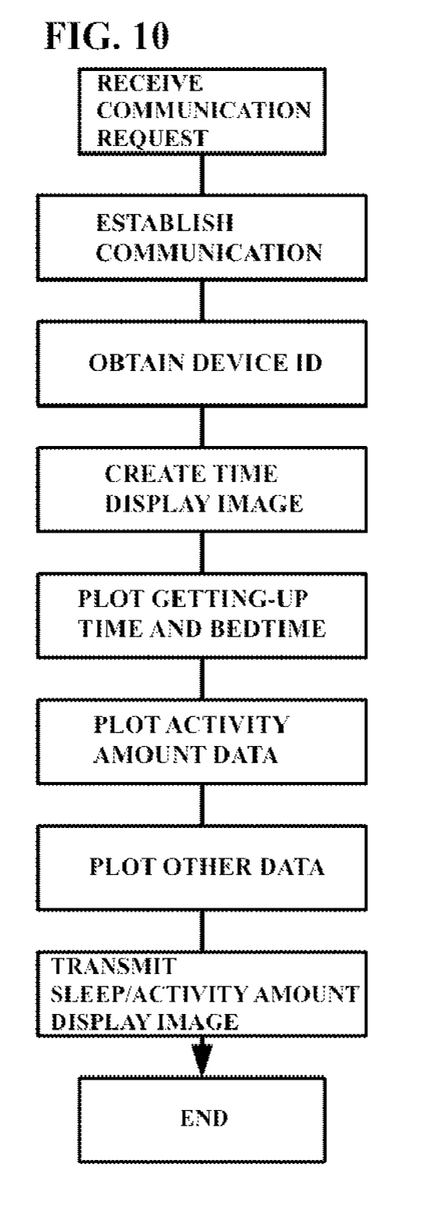
FIG. 10 is a diagram showing an example of an operation by which a server creates a sleep and activity amount display image.

A program executed by the server 14 (FIG. 1) of the present preferred embodiment includes a step of obtaining the sleep data from the sleep measurement device 12, a step of obtaining the activity amount data from the activity amount measurement device 13, a step of creating the sleep and activity amount display image, and a step of transmitting the sleep and activity amount display image to the display terminal 15. The step of creating the sleep and activity amount display image includes a step of creating the time display image and a step of plotting the sleep data, the activity amount data, and other data on the time display image. FIGS. 8 to 10 are examples of flowcharts showing basic operations of the program of the present preferred embodiment.

FIG. 8 shows operations up to when the server 14 establishes communication with the sleep measurement device 12 and obtains the sleep data. The server 14 establishes communication when a communication request is received from the sleep measurement device 12. When communication is established, the device ID and the like of the sleep measurement device 12 are obtained. The device ID of the sleep measurement device is linked with a user ID in advance, and by referencing a table stored in the memory 145, the user ID is obtained. Next, the sleep data is obtained, linked with the user ID, and stored in the memory 145.

FIG. 9 shows operations up to when the server 14 establishes communication with the activity amount measurement device 13 and obtains the sleep data. The server 14 establishes communication when a communication request is received from the activity amount measurement device 13. When communication is established, the device ID and the like of the activity amount measurement device 13 are obtained. The device ID of the activity amount measurement device 13 is linked with a user ID in advance, and by referencing a table stored in the memory 145, the user ID is obtained. Next, the activity amount data is obtained, linked with the user ID, and stored in the memory 145.

FIG. 10 shows operations up to when the server 14 creates the sleep and activity amount display image and transmits it to the display terminal 15. The server 14 establishes communication when a communication request is received from the display terminal 15. When communication is established, the device ID and the like of the display terminal 15 are obtained. The device ID of the display terminal 15 is linked with a user ID in advance, and by referencing a table stored in the memory 145, the user ID is obtained. Next, the type of graph, the display period, the length of the time slots, the type of data to be displayed, the display method, and the like are obtained by referencing a setting table that is linked to the user ID and stored in the memory 145. Next, a time display image divided into time slots that each indicate a predetermined range of time is created. Next, by referencing the data table that is linked to the user ID and stored in the memory 145, the getting-up time, bedtime, activity amount data, and other necessary data are obtained and plotted on the time display image. At this time, if the bedtime and getting-up time are not explicitly included in the sleep data stored in the memory 145, these times are obtained from data such as the sleep depth. Thus, when the sleep and activity amount display image is created, it is transmitted to the display terminal 15. The sleep and activity amount display image may be transmitted upon receiving a request from the display terminal 15. Also, the sleep and activity amount display image may be transmitted in a compressed form and displayed in an expanded form on the display terminal 15.

The present invention is not limited to the above-described preferred embodiment.

For example, in the above-described preferred embodiment, the server 14 (FIG. 1), on which a program for creating the sleep and activity amount display image is executed, and the display terminal 15 that presents the result to the user by display are configured separately. In contrast to this, in the case where the network 11 in FIG. 1 is a LAN, various information devices such as a personal computer or smartphone may be used as the server 14, and the sleep and activity amount display image may be displayed directly on the display screen thereof.

Also, for example, in the above-described preferred embodiment, the sleep and activity amount display image is created by the server 14 and transmitted to the display terminal 15. In contrast to this, the data for the image may be transmitted from the server 14 to the display terminal 15, and a visible image may be ultimately constructed by the display terminal 15.

Also, for example, in the above-described preferred embodiment, the server 14 obtains device IDs from the sleep measurement device 12, the activity amount measurement device 13, and the display terminal 15 and obtains user IDs based thereon. In contrast to this, the user IDs may be obtained directly from the respective devices.

Also, for example, a request to transmit the display image may be transmitted from a device other than the display terminal 15. Accordingly, upon receiving the request to transmit the display image from a smartphone or the like, the server 14 can transmit the sleep and activity amount display image using e-mail, or upload it to a website on the Internet.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A non-transitory computer-readable recording medium storing a sleep and activity amount display program for causing a computer to perform a method comprising:
   obtaining sleep data of a user from a sleep measurement device;
   obtaining activity amount data of the user from an activity measurement device;
   creating a time display image in the form of a wave with a period of 24 hours, divided into time slots that each indicate a predetermined range of time; and
   plotting a getting-up time and a bedtime included in the sleep data as well as the activity amount data on the time slots of the time display image; wherein
   the time display image is continuous, without interruption, such that the time display image proceeds downwardly with a progression of time to reach a low point at midnight, and then proceeds upwardly with the progression of time to reach a high point at noon of a next day; and
   the time display image is scrollable in a time direction.

2. The non-transitory computer-readable recording medium according to claim 1, wherein the method further comprises:
   obtaining meal data relating to a meal of the user; and
   plotting a meal time included in the meal data on the time slots of the time display image.

3. The non-transitory computer-readable recording medium according to claim 1, wherein the method further comprises:
   displaying a predetermined time range before the bedtime as a relax zone on the time slots of the time display image.

4. The non-transitory computer-readable recording medium according to claim 1, wherein
   the activity amount data is displayed in association with an area, number, or color of a graphic, or a combination thereof.

5. The non-transitory computer-readable recording medium according to claim 1, wherein
   the time display image is displayed such that a portion of a wave shape moving upward is before noon, and a portion moving downward is after noon.

6. A sleep and activity amount display device comprising:
   a controller; and
   a memory; wherein
   the controller obtains sleep data of a user from a sleep measurement device;
   the controller obtains activity amount data of the user from an activity measurement device;
   the controller creates a time display image in the form of a wave with a period of 24 hours, divided into time slots that each indicate a predetermined range of time; and
   the controller plots a getting-up time and a bedtime included in the sleep data as well as the activity amount data on the time slots of the time display image;
   the time display image is continuous, without interruption, such that the time display image proceeds downwardly with a progression of time to reach a low point at midnight, and then proceeds upwardly with the progression of time to reach a high point at noon of a next day; and
   the time display image is scrollable in a time direction.

7. A sleep and activity amount display system comprising:
   a server, a sleep measurement device, an activity measurement device, and a display terminal connected via a network, wherein
   sleep data of a user measured by the sleep measurement device is transmitted to the server and accumulated in the server,
   activity amount data of the user measured by the activity measurement device is transmitted to the server and accumulated in the server,
   the server creates a display image in the form of a wave with a period of 24 hours, divided into time slots that each indicate a predetermined time range, the display image displaying a getting-up time and a bedtime included in the sleep data, as well as the activity amount data on the time slots,
   the server creates the display image which is continuous, without interruption, such that the time display image proceeds downwardly with a progression of time to reach a low point at midnight, and then proceeds upwardly with the progression of time to reach a high point at noon of a next day;
   the time display image is scrollable in a time direction; and
   the display image created by the server is transmitted to the display terminal and is displayed on the display terminal.

8. A sleep and activity amount display method comprising:
   obtaining sleep data of a user from a sleep measurement device;
   obtaining activity amount data of the user from an activity measurement device;
   creating a time display image in the form of a wave with a period of 24 hours, divided into time slots that each indicate a predetermined range of time; and
   plotting a getting-up time and a bedtime included in the sleep data as well as the activity amount data on the time slots of the time display image; wherein
   the time display image is created such that the time display image is continuous, without interruption, such that the time display image proceeds downwardly with a progression of time to reach a low point at midnight, and then proceeds upwardly with the progression of time to reach a high point at noon of a next day; and the time display image is scrollable in a time direction.

* * * * *